(12) United States Patent
Rapheal

(10) Patent No.: US 6,267,564 B1
(45) Date of Patent: Jul. 31, 2001

(54) MEDICAL RESERVOIR BAG AND SYSTEM

(75) Inventor: John R. Rapheal, St. Paul, MN (US)

(73) Assignee: SIMS Deltec, Inc., St. Paul, MN (US)

( * ) Notice: Subject to any disclaimer, the term of this patent is extended or adjusted under 35 U.S.C. 154(b) by 0 days.

(21) Appl. No.: 09/310,608

(22) Filed: May 12, 1999

(51) Int. Cl.$^7$ ............................................. F04B 53/00
(52) U.S. Cl. ........................ 417/234; 604/153; 604/262; 604/408; 604/415
(58) Field of Search ........................... 417/234; 604/153, 604/403, 408, 415, 257, 262

(56) References Cited

U.S. PATENT DOCUMENTS

| | | | |
|---|---|---|---|
| 2,062,040 | 11/1936 | Rigney | 206/69 |
| 2,273,128 | 2/1942 | Madsen et al. | 150/2.1 |
| 2,378,719 | 6/1945 | Madsen et al. | 128/229 |
| 2,816,596 | 12/1957 | Welch, Jr. | 154/42 |
| 2,850,422 | 9/1958 | Welch, Jr. | 154/118 |
| 2,949,712 | 8/1960 | Bieberdorf et al. | 53/29 |
| 3,030,955 | 4/1962 | Gossett et al. | 128/272 |
| 3,177,871 | 4/1965 | Meyers | 128/227 |
| 3,244,576 | 4/1966 | Swartz | 156/513 |
| 3,298,597 | 1/1967 | Bellamy | 229/55 |
| 3,343,541 | 9/1967 | Bellamy | 128/272 |
| 3,403,064 | 9/1968 | Bellamy | 156/273 |
| 3,554,256 | 1/1971 | Anderson | 150/8 |
| 3,642,047 | 2/1972 | Waage | 150/8 |
| 3,901,235 | 8/1975 | Patel et al. | 128/275 |
| 3,915,212 | 10/1975 | Bujan et al. | 150/8 |
| 4,332,252 | 6/1982 | Taylor | 128/275 |
| 4,484,904 | 11/1984 | Fowler | 493/213 |
| 4,535,820 | 8/1985 | Raines | 137/854 |
| 4,609,369 | 9/1986 | Ball | 604/56 |
| 4,619,648 | 10/1986 | Rath et al. | 604/326 |
| 4,636,412 | 1/1987 | Field | 428/35 |
| 4,683,916 | 8/1987 | Raines | 137/854 |
| 4,906,495 | 3/1990 | Martini et al. | 428/36.7 |
| 4,950,347 | 8/1990 | Futagawa | 156/272.4 |
| 4,959,062 | 9/1990 | Gellman | 604/403 |
| 5,176,634 | 1/1993 | Smith et al. | 604/87 |
| 5,226,564 | 7/1993 | Steer et al. | 222/107 |
| 5,391,150 | 2/1995 | Richmond | 604/111 |
| 5,405,333 | 4/1995 | Richmond | 604/257 |
| 5,445,623 | 8/1995 | Richmond | 604/251 |
| 5,507,904 | 4/1996 | Fisher et al. | 156/252 |
| 5,540,561 | 7/1996 | Johnson | 417/234 |
| 5,567,119 | * 10/1996 | Johnson | 417/53 |
| 5,591,337 | 1/1997 | Lynn et al. | 210/489 |
| 5,645,538 | 7/1997 | Richmond | 604/256 |
| 5,735,826 | 4/1998 | Richmond | 604/251 |
| 5,772,409 | * 6/1998 | Johnson | 417/360 |
| 5,772,880 | 6/1998 | Lynn et al. | 210/435 |
| 5,785,700 | 7/1998 | Olson | 604/408 |
| 5,820,582 | * 10/1998 | Keilman | 604/49 |
| 5,848,994 | 12/1998 | Richmond | 604/248 |
| 6,196,991 | * 3/2001 | Keilman | 604/29 |

\* cited by examiner

*Primary Examiner*—Timothy S. Thorpe
*Assistant Examiner*—Ehud Gartenberg
(74) *Attorney, Agent, or Firm*—Merchant & Gould P.C.

(57) ABSTRACT

A bag arrangement for containing fluid for use with an infusion pump. The bag arrangement includes a first end and a second end, and includes a panel defining a interior chamber. The arrangement further includes a fluid outlet port in the panel, the outlet port in fluid communication with the interior chamber. An elongated hollow member is in fluid communication with the port, and extends from the first end toward the second end of the bag arrangement tangentially along the panel.

18 Claims, 5 Drawing Sheets

MEDICAL RESERVOIR BAG AND SYSTEM

FIELD OF THE INVENTION

The present invention relates to flexible bags for use in medical infusion systems, and more particularly to flexible bags for use with infusion pump systems.

BACKGROUND OF THE INVENTION

Infusion systems are known which include a flexible bag as a fluid reservoir, a pump for pumping fluid from the bag to a patient, and a tubing from a bag to the pump and from the pump to the patient for transporting the fluid. Typically the bag is a flexible bag made from polymeric material, and the pump is an infusion-style pump designed to deliver a premeasured fluid drug dose at a given rate to the patient in need of the drug.

The bag may be hung from a pole or carried in an enclosure. Various enclosures are known including flexible pouches and more rigid enclosures. U.S. Pat. Nos. 5,540,561 and 5,567,119, the disclosures of which are incorporated herein by reference, concern rigid enclosure arrangements designed to protect fluid reservoirs. These enclosure arrangements include a chamber for receiving a fluid reservoir such as a flexible bag. The enclosures each include an opening for accessing the chamber. The enclosures each further include a latch arrangement for mounting an ambulatory pump to the enclosure to protect the reservoir and tubing.

These enclosures have a number of advantages as enumerated in U.S. Pat. Nos. 5,540,561 and 5,567,119. For example, flexible fluid reservoirs prepared from the polymeric materials are capable of being punctured or torn by sharp objects. This can be a problem for patients who use the pumps outside the hospital or caregiver's office. This creates a particular problem when the fluid contained within the bag is irritating to the skin or where the fluid contains a controlled substance. Where the fluid contained within the bag is a controlled substance, such as a narcotic, the enclosures prevent the controlled substance from being withdrawn from the bag by a needle punctured through the polymeric material or the tubing.

U.S. Pat. No. 5,879,143, the disclosure of which is herein incorporated by reference, concerns adapters designed to secure an infusion-type pump to an enclosure such that the enclosures discussed above may be used with a wide variety of pump sizes and shapes.

Many of the known flexible medical bags, for use in such infusion systems include outlet ports at their lower peripheral edge. Such arrangements may be problematic in that the enclosure arrangements used to protect the bags are sized to accommodate the peripheral space taken by the structure of the outlet port. Furthermore, the peripheral ports are more likely to present problems regarding occlusion. Often times, additional structure such as a bag post is included within the enclosure arrangement to hold the bag and thereby prevent the bag from laying on or otherwise occluding the fluid outlet port, or the tubing leading to the fluid outlet port.

There is a need for a flexible bag arrangement to address these concerns. It is desirable that the bag arrangement is usable within infusion systems having enclosure arrangements. It is also desirable that the bag arrangement allow for smaller enclosures in the enclosure arrangements, and that the bag provide for protection against occlusion without the need for additional structure within the enclosure arrangement.

SUMMARY OF THE INVENTION

One aspect of the present invention relates to a bag arrangement for containing fluid for use with an infusion pump. The bag arrangement includes a first end and a second end, and includes a panel defining a interior chamber. The arrangement further includes a fluid outlet port in the panel, the outlet port in fluid communication with the interior chamber. An elongated hollow member is in fluid communication with the port, and extends in a direction from the first end toward the second end of the bag arrangement tangentially along the panel.

In one embodiment, the bag arrangement includes a bag having a first wall and a second wall defining an interior chamber. The bag has a first end and a second end, and a fluid outlet port through the first wall in fluid communication with the interior chamber. The fluid outlet port includes an elongated hollow member extending through an opening in the first wall, and is oriented tangentially to the first wall. The elongated hollow member extends from within the interior chamber from the first end of the bag, through the opening, and toward the second end of the bag along the first wall. Preferably, the hollow elongated member is a tube, and the first wall is formed by two segments sealed around the tube at the port. The tube is also preferably attached to the first wall within the bag.

Another aspect of the invention relates to a pump system. The pump system includes an enclosure arrangement defining a chamber, the chamber accessible through an opening. A pump is mounted to the enclosure arrangement to close the opening to the chamber. A bag arrangement containing fluid is located in the chamber. The bag arrangement includes a panel defining a interior chamber, and the bag arrangement includes a first end and a second end. A fluid outlet port is in the panel, and the outlet port is in fluid communication with the interior chamber. An elongated hollow member is in fluid communication with the port, and extends in a direction from the first end toward the second end of the bag arrangement. The pump system further includes a fluid conduit arrangement to provide a fluid path to the pump. The pump may include an adapter for mounting the pump to the enclosure so as to close the opening to the enclosure.

DETAILED DESCRIPTION OF THE PREFERRED EMBODIMENTS

Figure 1:
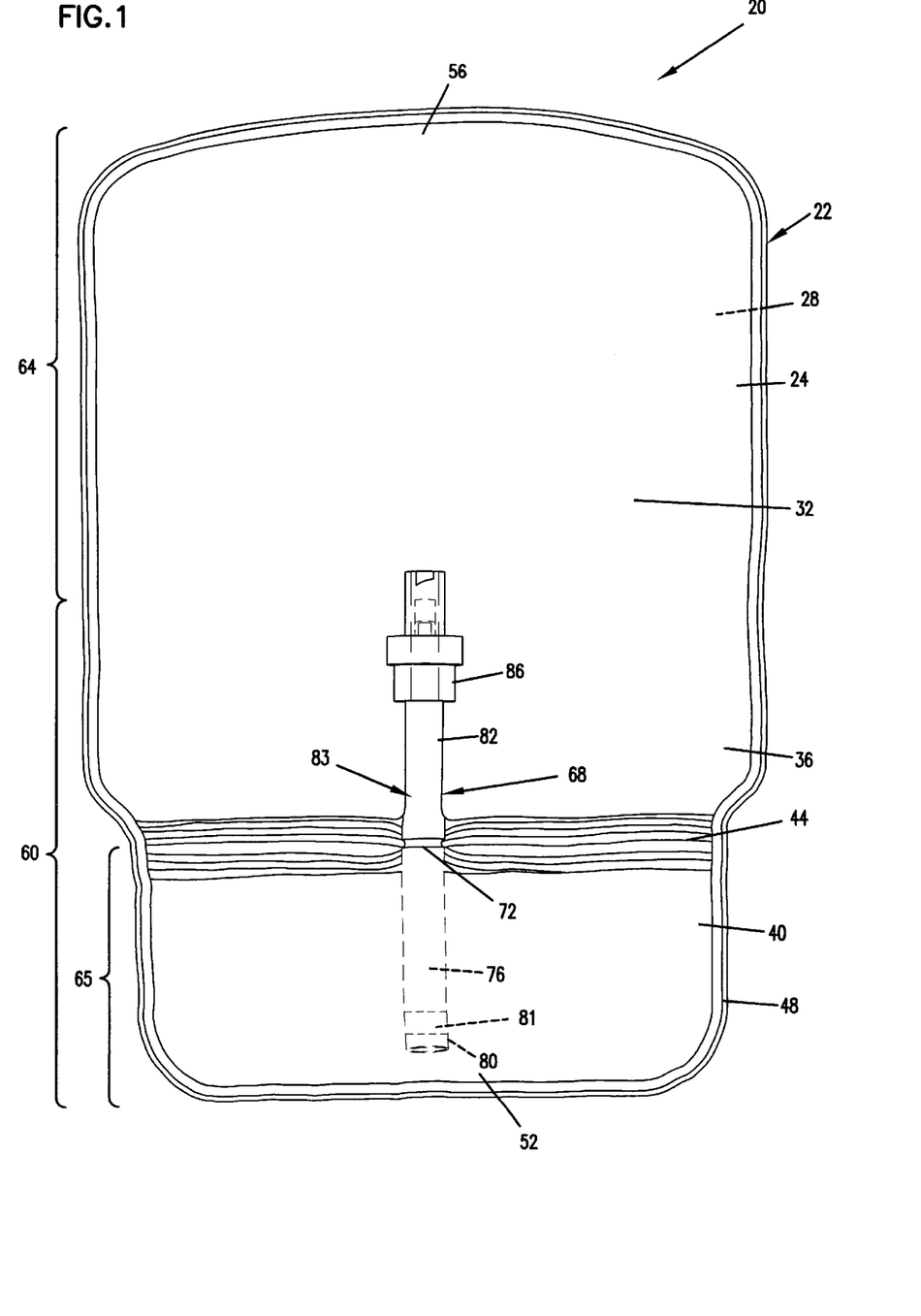
FIG. 1 is a front view of one embodiment of a bag arrangement according to the invention.

Referring to FIG. 1, an embodiment of a bag arrangement 20 is shown. The bag arrangement 20 includes a bag 22 having a flexible panel arrangement defining sides of the bag for enclosing fluid. In the embodiment shown, bag 22 has first and second panels or walls 24 and 28 that define an interior chamber 32. The walls 24, 28 are preferably made of flexible material, such as a polymer material. First wall 24 is made of flexible wall sections or segments 36 and 40 which overlap slightly and are joined together at a lateral seal 44. The second wall 28 is made of one continuous sheet of flexible material. The first and second walls 24 and 28 are joined together at a peripheral seal 48 to form bag 22 having interior chamber 32. The lateral seal 44 and peripheral seal 48 are created with methods or apparatus for sealing flexible material together as generally known in the art. For example, the seals can be created with Radio Frequency (RF) welding, heat sealing, the use of adhesives, or any other methods generally known for sealing flexible members together.

The bag includes a first end 52, a second end 56, a first half 60, and a second half 64. The first half 60 extends generally from a point about one half of the distance between the first and second ends to the first end 52. The second half 64 extends from a point located about one half of the distance between the first and second ends, to the second end 56. The first half 60 of the bag 22 includes a narrow portion 65 adjacent the first end 52 of the bag 22.

The bag arrangement 20 further includes a fluid outlet port 68 in fluid communication with the interior chamber 32. The port 68 extends through an opening 72 in the first wall 24. In the embodiment shown, the opening 72 is located generally along seam 44, however this is not necessary. The opening 72 is sealed around the port 68 to create a fluid tight seal around the port 68. Preferably the opening 72, and therefor the port 68, are located in the first half of the bag 22. Port 68 preferably includes an elongated hollow tube construction. A first portion 76 of elongated hollow tubing is located within the interior chamber 32, and extends from a point adjacent the first end 52, tangentially along an inside of wall 24, generally in a direction towards the second end 56 of bag 22, and ends at the opening 72. The first tube portion 76 provides for fluid communication between the interior chamber 32 and the opening 72. The first portion 76 of tubing includes a tubing first end 80 spaced apart from the opening 72. Preferably, the tubing first end 80 is coupled to the wall 24 adjacent the first end 52 of the bag such that the first portion 76 of the tubing is maintained in a generally straight arrangement from the tubing first end 80 to the opening 72, tangentially along wall 24. The end 80 may be coupled to the wall with methods or with apparatus generally known in the art. In one embodiment, the end 80 is coupled to the wall 24 through RF welding at weld 81. A second portion 82 of hollow elongated tubing extends from the opening 72 externally from the interior chamber 32 tangentially along an outside of wall 24, generally from the port towards the second end 56 of bag 22. Weld 81 and the tube extending through opening 72 and sealed to the bag wall at that location create added stiffness for a lower end of bag arrangement 20.

In the embodiment shown, the port 68, and the first and second portions 76, 82 of elongated hollow tubing are one continuous piece of elongated hollow tubing 83 extending from a point adjacent the first end 52, tangentially along wall 24, through the opening 72 in the wall 24, and generally in a direction towards the second end 56. To construct the bag arrangement, the continuous piece of elongated tubing 83 is inserted between overlapping wall segments 36 and 40 at the desired location of the port 60 prior to forming seal 44. Seal 44 is then created, as discussed above, through the use of RF welding, heat sealing, adhesives, or other methods generally known in the art. The seal 44 creates a fluid tight seal around the port 68, which is thereby formed rigidly into the wall 24. Preferably seal 44 and weld 81 are formed at the same time to form wall 24 and port 68. Then wall 24 is sealed to wall 28 via the RF weld or other technique. In other embodiments, where the opening 72 is not within the seal 44, an opening can be provided in wall 24, the tube 83 can be positioned in the opening and sealed into the wall using an appropriate sealing method. Opening 72 may also be provided in seal 48.

As discussed above, the walls 24, 28 are preferably made of flexible material, such as a polymer material, for example a thermoplastic polymer material. One example of a suitable thermoplastic polymer material is a PVC film, preferably with non-DEHP TOTM plasticizer, commercially available from Ellay, Inc under the product name EH-222 PVC film. This film has a thickness of about 0.015 inches, and has a taffeta (textured) pattern on the inside and a matte surface (smooth) on the outside. The elongated tubing 83 is preferably made of a polymer material, for example a thermoplastic polymer material. One suitable material for the tubing is commercially available from Colorite/Unichem Plastics under the product name Unichem 7477G-015, with gamma resistant, non-DEHP TOTM plasticizer. One suitable tubing has an inner diameter of about 0.155 inches (+/−0.004 inches), and outer diameter of about 0.240 inches (+/−0.004 inches), and a durometer of about 74 (+/−3), Shore A, 15s.

The bag arrangement 20 further includes a fluid conduit connector 86 in fluid communication with the second portion 82 of elongated hollow tubing. The fluid conduit connector 86 may be any type of fluid conduit connector generally known in the art. In the embodiment shown, the fluid conduit connector 86 comprises a Luer activated valve. Suitable valves for use as the fluid conduit connector 86 are disclosed in U.S. Pat. No. 4,535,820 and 4,683,916, the disclosures of which are herein incorporated by reference.

Figure 2:
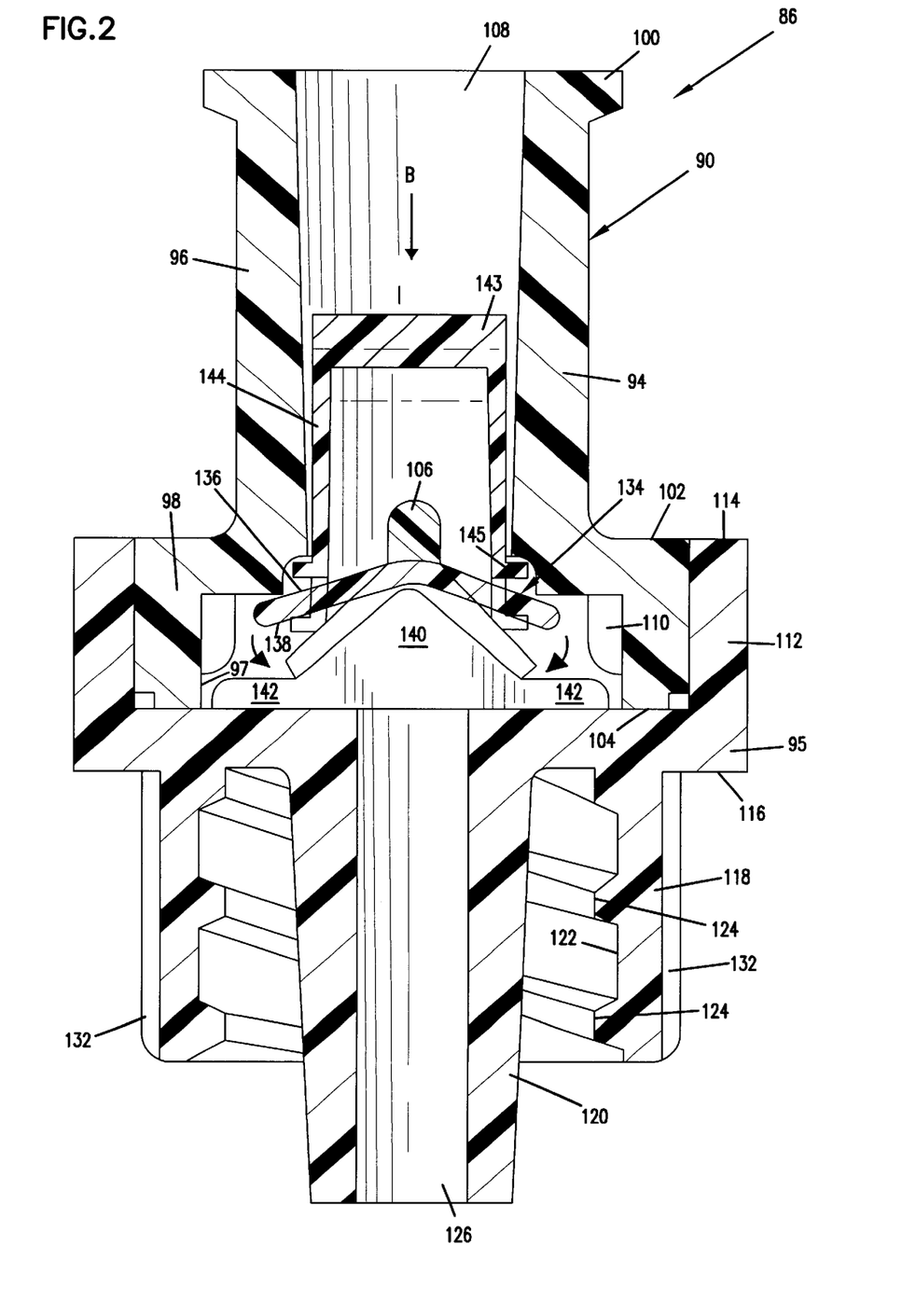
FIG. 2 is a cross-sectional view of the Luer activated valve of the bag arrangement shown in FIG. 1.

Referring now to FIG. 2, one particular Luer activated valve 90 is disclosed that may be used as the fluid conduit connector 86. The Luer activated valve 90 is a bi-directional, normally closed check valve. The valve 90 includes a valve body made of first and second body elements 94 and 95. First element 94 has a tubular portion 96 terminating in an enlarged container 98. Locking ears 100 are provided at one end of the tubular portion 96, for locking the valve with a valve activator/colmector to connect the valve to a pump through an associated fluid conduit, as will be discussed below. The container portion 98 has an upper surface or shoulder 102 and lower surface 104. A traverse crossbar 106 is formed within this element, with the axis thereof being in line with the surface 102. A longitudinal inlet opening 108, preferably having a female taper, extends through tubing 96 into the interior of container 98. The inner circumferencial wall 97 of the container 98 is provided with the plurality of longitudinally extending ribs 110. These ribs are for preventing binding of the peripheral edge of the flexible valve disc 134 as contained within the body portion of the valve after arrangement with the second body element 95.

The second body element 95 for the valve comprises a can 112 having an upper surface 114 and a lower shoulder 116, integral with a double tubular extension 118 and 120. Within the outer tubing portion 118 is an inner wall 122 provided with threads 124 for attachment to a tube. The central tubular portion 120 is provided with an inner outlet opening 126 therethrough and an outer male Luer taper. Recesses 132 also are provided in the outer circumference of outer tubular portion 118. In the bag arrangement 20 shown in FIG. 1, tube portion 82 is slid onto and surrounds the central tubular portion 120, and the threads 124 of the outer tubing portion 118 engage the tube portion 82 to attach the Luer activated valve 90 to the second portion 82 of elongated hollow tubing.

Referring again to FIG. 2, the valve disc 134 is a circular disc provided with opposite surfaces 136 and 138 both of which are substantially flat. The disc 134 preferably is made of flexible yet resilient rubber or rubber-like material. A triangular pointed member 140 having extending ribs 142 therewith is molded or integrally affixed to the can 112 of the second body element 112. When the flexible disc 134 is completely open, as indicated by the dotted lines, an adequate space will open for liquid flow about the peripheral edge of the disc 134.

An additional member is included with the foregoing elements for the purpose of permitting opening of the valve disc 134. This member comprises a circular ring 143 having integrally formed legs 144 extending therefrom. The tip edges of these legs are provided with enlarged ribs 145 at the free ends thereof. In a normal position the valve disc 134 will be closed as shown in FIG. 2, however, upon engagement of the rings 143 by a male Luer element, a user of the device can push the member in the direction of arrow B to open the valve disc 134. The dotted lines in FIG. 2 show this valve disc as opened.

The bag arrangement 20, having the fluid outlet port and the tube members extending tangentially along the wall 24 from the first end toward the second end of the bag, allows for the bag arrangement to take up a smaller amount of peripheral space than prior bag arrangements. This is an advantage when such bag arrangements are used in a pump system where the bag arrangement is stored in an enclosure. Additionally, this unique bag arrangement 20 provides for easy connection to a pump, while reducing the possibility of occlusion of the tubing material extending from the bag arrangement 20 to the pump.

Figure 3:
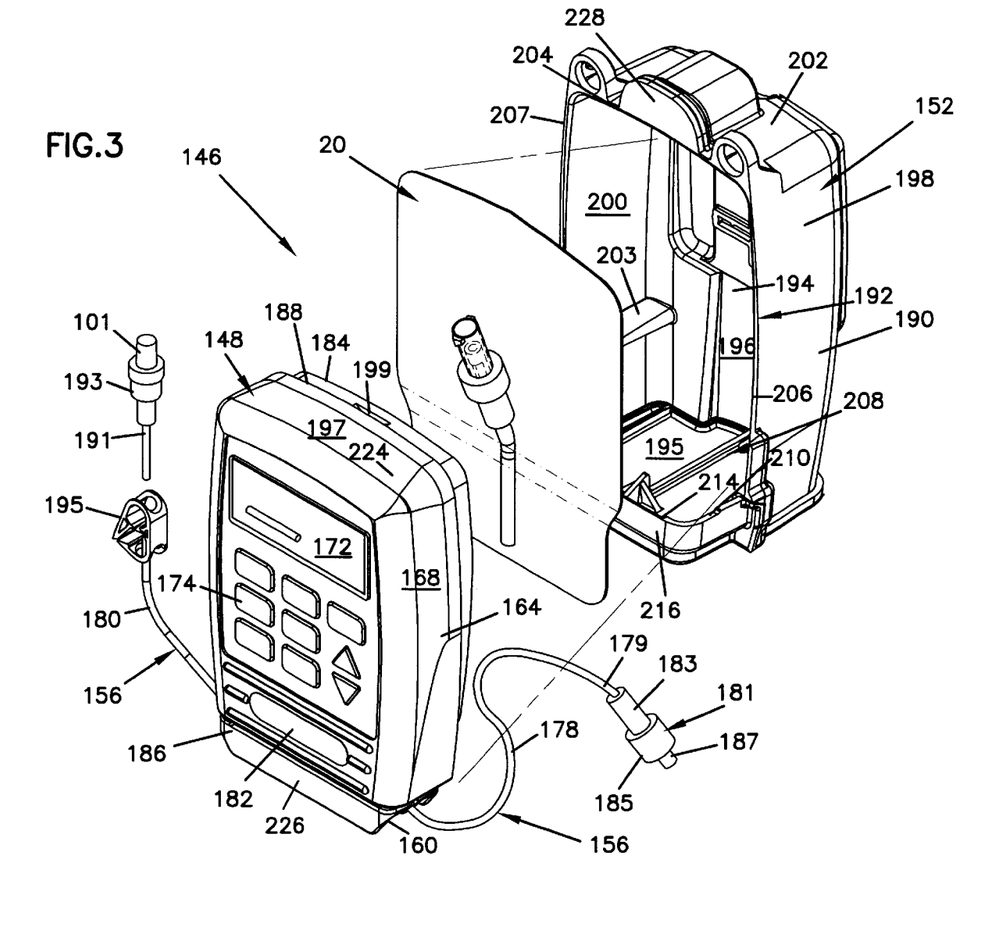
FIG. 3 is a partially exploded perspective view of one embodiment of a pump system incorporating the bag arrangement shown in FIG. 1.

Referring now to FIG. 3, a first embodiment of a pump system 146 includes a pump 148, a bag arrangement 20, and an enclosure arrangement 152. The system 146 also includes an associated fluid conduit arrangement 156 for connecting the bag arrangement 20 to the pump 148, and the pump 148 to the patient during use.

As shown in FIG. 3, the pump 148 includes a pressure plate 160 which is selectively mounted to a control module 164. Pressure plate 160 has a generally planar top surface for use in the pumping operation as will be described later. Control module 164 includes a control module outer housing 168, a display 172 and a keypad 174. A pump mechanism (not shown) engages a portion of the fluid conduit arrangement 156 passing between control module 164 and the top planar surface of pressure plate 160. An example of a pump mechanism is described in U.S. Pat. No. 4,559,038, issued Dec. 17, 1985, to Berg et al., the disclosure of which is incorporated herein by reference. The pump mechanism disclosed in the U.S. Pat. No. 4,559,038 includes a rotatable cam shaft, and three reciprocally mounted followers (inlet valve, expulsor, and outlet valve) which engage a tube in a predetermined manner to pump fluid through the tube. The cam shaft is rotated to cause fluid to be pumped to the patient. Another example of a pump mechanism with a double lobed cam shaft is disclosed in U.S. Pat. No. 5,364, 242, issued Nov. 15, 1994, to Olson, the disclosure of which incorporated herein by reference. Those of ordinary skill in the art will recognize that other pump mechanisms may be used with the invention, such as a wave style mechanism, or a rotary or a roller style mechanism.

U.S. Pat. No. 4,559,038 also discloses one example of selectively mounting structure for mounting pressure plate 160 to control module 164, including two hooked portions, two hinge pins, and an inverted U-shaped member, where the hook portions extend from the pressure plate and cooperate with the two hinge pins on the control module, and the U-shaped member is engaged by latcl/lock structure on the control module.

The bag arrangement 20 is interconnected to pump 148 via fluid conduit arrangement 156. A first tube portion 178 connects bag arrangement 20 to pressure plate 160. Specifically, the first tube portion 178 has a first end 179 including a Luer valve activating/connecting member 181. The activating/connecting member 181 includes a hollow tube connector portion 183, a connector outer housing 185 and an inner Luer activator member 187. The end 179 of tube portion 178 fits within and is coupled to the hollow tube connector portion 183. The tube connector member is in fluid communication with the activator member 187. The activator member fits within the inlet opening 108 of the Luer activated valve 90 of the bag arrangement, and engages the ring 143 to open valve disc 134. The locking ears 100 engage threads (not shown) located on the inner surface of the connector outer housing 185 to secure the activating/connector member 181 to the valve 90. The activating member engages the Luer activated valve 90 of the bag arrangement 20 such that the bag arrangement 20 is in fluid communication with the first tube portion 178. It should be understood by those of skill in the art that a broad variety of connector members or valves may be used to interconnect the bag arrangement 20 and a pump, and that the invention is in no way limited to the specific connector members and valves illustrated and described above.

A second tube portion 180 extends from pressure plate 160 to the patient. In the embodiment shown, the second tube portion 180 has a tube portion second end 191 having an activating/connecting member 193 attached thereto. The connector member 193 is substantially the same as connected member 181, and can be used to connect with liquid delivery devices, such as additional tubing, or needles, or other structures generally known for delivering liquid to a patient. A removable cap 101 is also shown on the connecting member 193, which acts to cover and protect the connecting member 193 when it is not in use. A pinch clamp 195, as generally known in the art, is also shown. A third tube portion (not shown), located between the first two tube portions 178 and 180, is engaged by pump mechanism to cause pumping of the fluid. Third tube portion is sized to pump the appropriate amount of fluid for activation of pump mechanism.

Pump 148 includes a front surface 182 and a back surface 184. Front surface 182 includes a generally linear front ridge 186 protruding therefrom which cooperates with enclosure 152 to mount pump 148 to enclosure 152. The back surface 184 includes a ridge 188 for cooperating with enclosure 152 to mount pump 148 to enclosure 152. The ridge 188 needs sufficient structure to cooperate with enclosure 152 to permit mounting of the pump 148 to the enclosure 152 and to limit access to the bag arrangement 20. Likewise, pressure plate 160 of the pump 148 includes a bottom surface for cooperating with reciprocally shaped structure on the enclosure 152 during mounting of pump 148 to enclosure 152. A top surface 197 of the pump includes a slot 199 for cooperating with a latch structure that may be included on the enclosure, to mount the pump to the enclosure as will be discussed below.

Enclosure 152 includes a wall construction or housing 190 defining structure for a receiving bag arrangement 20 and structure for receiving pump 148. Edge 192 of wall construction 190 defines an opening into an interior of enclosure. Enclosure 152 defines a chamber 194 for receiving the bag arrangement 20. Chamber 194 is defined by a back panel 196, two side panels 198, 200 interconnected to back panel 196, and a top panel 202 interconnected to back panel 196 and both side panels 198, 200. During use, bag arrangement 20 is positioned within chamber 194 and enclosed by the back surface 184 of the pump 148. Narrow portion 65 of bag arrangement 20 fits in narrowed portion 195 of enclosure defined by support ribs 203.

In chamber 194, bag arrangement 20 is protected from tears or punctures. Similarly, the first tube portion 178 of fluid conduit arrangement 156 is protected. In addition, enclosure 152 provides convenient structure for maintaining bag arrangement 20 in close proximity to pump 148 in a manner that is easy for the patient to handle in transport.

Edge 192 of enclosure 152 includes a top edge portion 204 and two side portions 206, 207. Ridge 188 on the pump 148 fits within that periphery defined by the top edge portion 204 and side edge portions 206, 207. Edge 192 includes a bottom edge portion 208 comprising two opposed sides 210, (one of which is not shown) and a front portion 214. The side portion that is not shown defines a slot for receipt of second tube portion 180 as it extends from pump to the patient.

Enclosure 152 includes a retaining lip 216 mounted near front portion 214 of edge 192. A portion of the first end 226 of pump 148 fits within the interior of enclosure 152 adjacent retaining lip 216. A portion of the front surface 182 of pump 148 is positioned inside retaining lip 216 of enclosure 152.

At the opposite or second end 224 of the pump 148 adjacent the top surface 197, enclosure 152 may include a latch arrangement (not shown) for holding the second end 224 of pump 148 while the first end 226 of pump 148 is held by retaining lip 216. In one embodiment, a rotatably mounted detent or projection fits into a slot or recess 199 in the top surface 197 of pump 148. A cover plate 228 covers an opening in the housing of the enclosure wherein the detent may be housed, for protecting and limiting access to the detent. A rotatably mounted shaft permits rotation of the detent into and out of engagement with the slot 199 of the pump 148. When it is desired to access the chamber 194 to remove bag arrangement 20, such as when the bag arrangement 20 is empty or is to be changed, the shaft to the latch arrangement is turned to release the second end 224 of the pump from the enclosure 152. The pump 148 is then separable from the enclosure 152.

Other latch arrangements are possible for selectively holding the second end 224 to the enclosure 152. Any appropriately configured structure for selectively gripping, holding, or trapping structure on pump 148 is usable. For example, a loop (not shown) could extend from pump 148 and a latch arrangement on the enclosure could include a hook (not shown) for holding the loop. Alternatively, a hook shaped recess (not shown) in pump 148 could be engaged by a hook on the enclosure (not shown), extending from a latch arrangement. It is also to be appreciated that any of the possible latch arrangements could be reversed in configuration. For example, a detent could be pivotably mounted to the pump and the slot could be positioned in the wall construction of the enclosure.

The enclosure is preferably made for a polymeric material, preferably molded plastic and preferably at least partially transparent to light to permit viewing of the contents of the chamber, such as PVC or polycarbonate.

Once the pump 148 is positioned to close the opening defined by the edge 192 of the enclosure 152, the bag arrangement 20 contained within the chamber is protected.

Needle access to the bag arrangement 20 is prevented due to the ridge 188 and retaining lip. Also, the fluid conduit arrangement 178 is protected.

The bag arrangement 20, having the fluid outlet extending along the wall 24 from the first end toward the second end of the bag allows for a smaller enclosure area than in prior arrangements. Additionally, this bag arrangement 20 provides for easy connection to a pump, while reducing the possibility of occlusion of the tubing material extending from the bag arrangement 20 to the pump.

Figure 4:
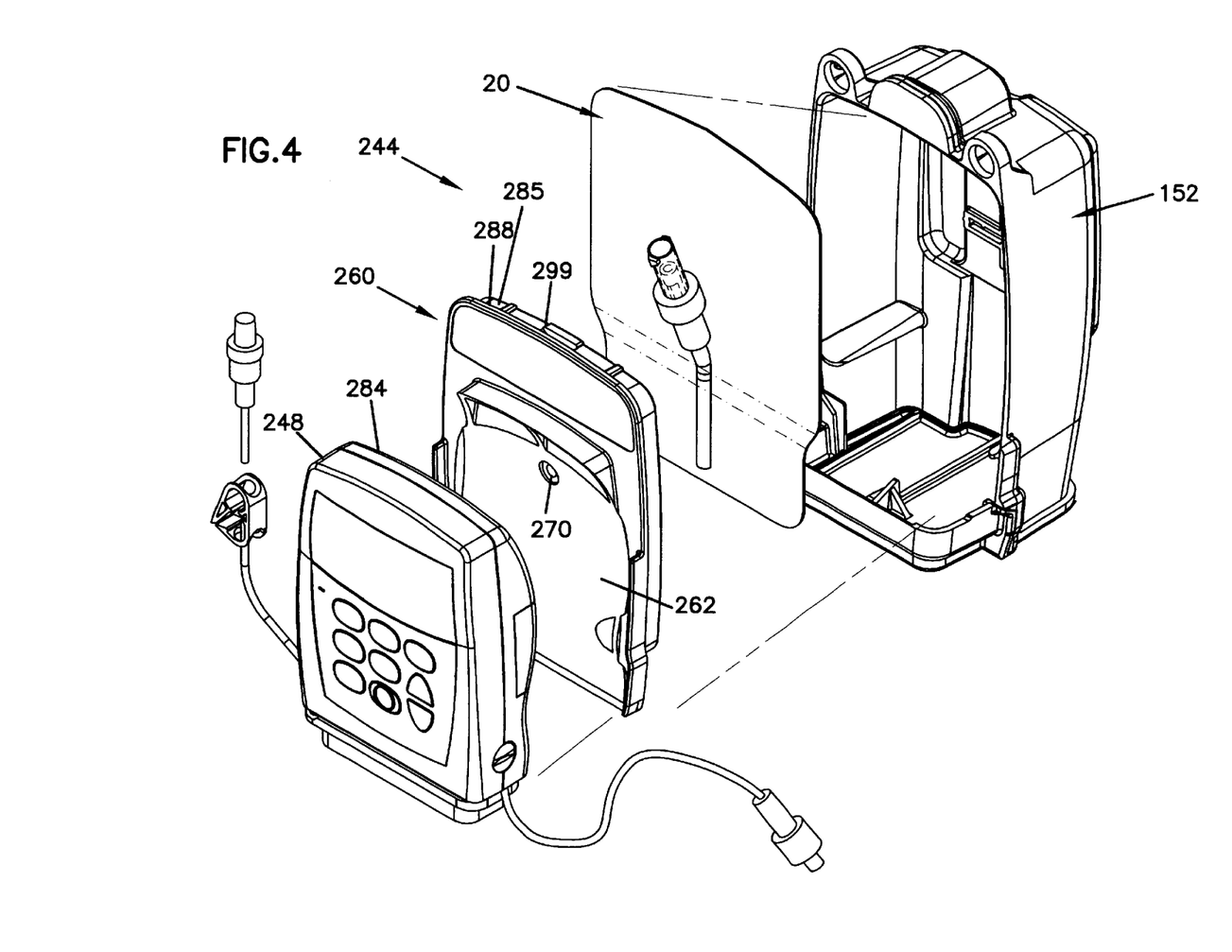
FIG. 4 is a partially exploded perspective view of another embodiment of a pump system incorporating the bag arrangement shown in FIG. 1.

Referring now to FIG. 4, a second embodiment of a pump system 244 is shown. The pump system 244 includes a pump 248, a bag arrangement 20, an enclosure arrangement 152 and an associated fluid conduit arrangement 156. The bag arrangement 20, the enclosure arrangement 152 and the fluid conduit arrangement 156, in this embodiment are substantially the same as those shown and discussed above in the first embodiment of a pump system 146. The pump 248 has a similar function and mechanism as the pump 148 discussed above in the first embodiment, but has a generally different shape and size, and therefore cannot fit precisely within the opening of the enclosure 152 to completely close the opening. Therefore an adapter member 260 is provided. As discussed in the background of the invention, suitable adapters are disclosed in U.S. Pat. No. 5,879,143, the disclosure of which has been incorporated herein by reference.

In the embodiment illustrated in FIG. 4, the adapter member 260 includes a front face portion 262 which is adapted to engage the back surface 284 of the pump 248. The front face portion 262 is generally concave in shape, and is adapted to engage the generally convex shape of the back surface 284 of the pump 248. The adapter member 260 is attached to the back surface of the pump 248 by any attachment mechanism as generally known in the art. In the embodiment shown, a connector member, such as a screw or bolt, extends through an opening 270 in the adapter member, and into a corresponding threaded opening in the back surface 284 of the pump 248 to attach the pump 248 to the adapter member 260. The pump and adapter member fit within the opening of the enclosure 152 in a similar fashion as discussed above on the first embodiment, however the adapter member 260 acts as the back surface of the pump 248 such that the pump 248 is mounted securely to the enclosure, and access to the chamber of the enclosure is limited. The adapter member 260 includes a ridge 288 for cooperating with enclosure 152 to mount pump 248 and adapter member 260 to enclosure 152. Ridge 288 needs sufficient structure to cooperate with enclosure 152 to permit secure mounting of pump 248 and adapter 260 to enclosure 152 and limit access to bag arrangement 20. A top surface 285 of adapter member may include a slot 299, similar to the slot 199 of the pump 148 in the first embodiment, for corresponding with a latch structure that may be included on the enclosure 152 to mount the pump 248 and adapter 260 to the enclosure 152. Suitable latch arrangements include latch arrangements as discussed in the first embodiment.

Figure 5:
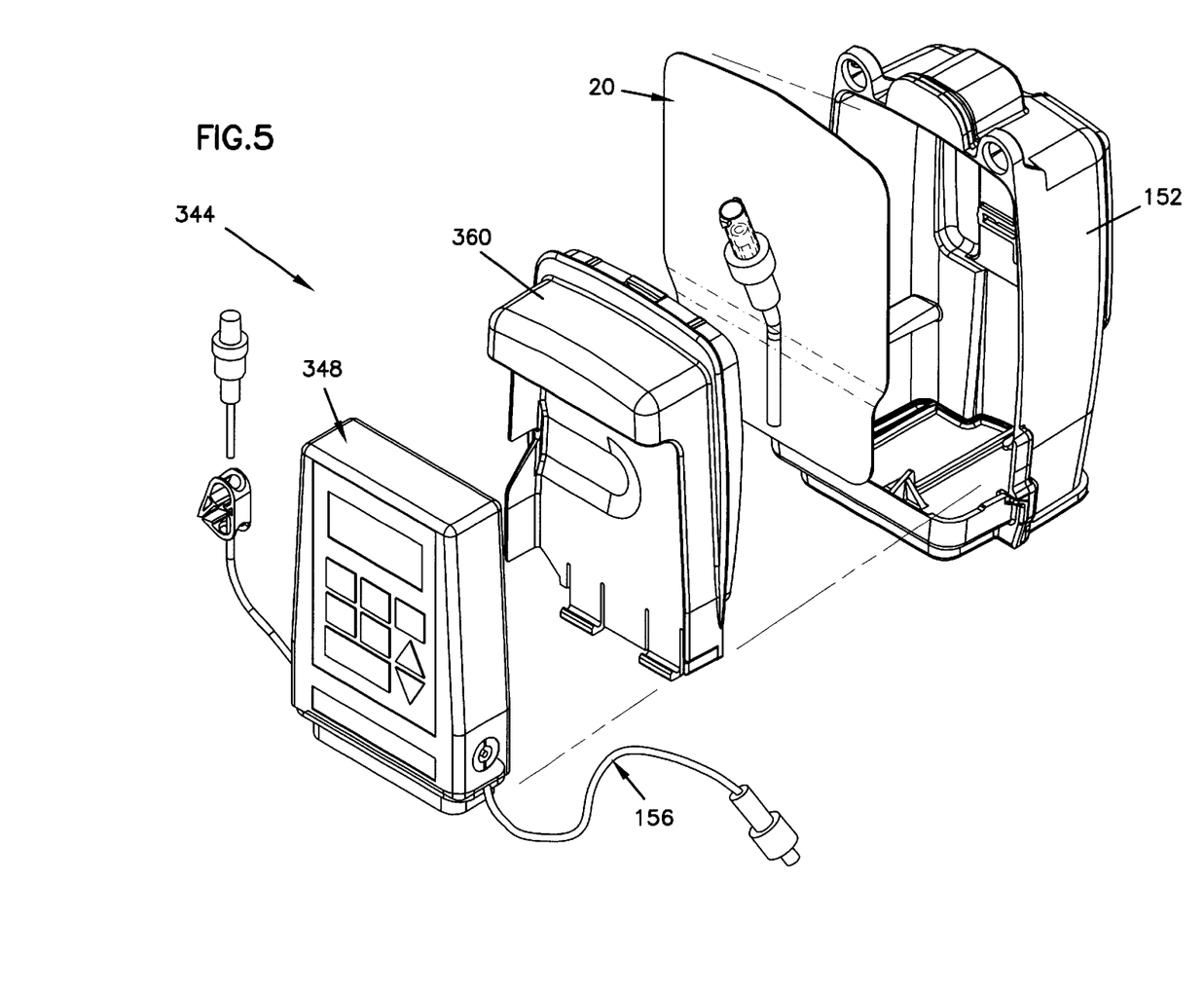
FIG. 5 is a partially exploded perspective view of yet another embodiment of a pump system incorporating the bag arrangement of FIG. 1.

Referring now to FIG. 5, a third embodiment of a pump system 344 is disclosed. The pump system 344 includes a pump 348, a bag arrangement 20, an enclosure arrangement 152 and a fluid conduit arrangement 156. The bag arrangement 20, the enclosure arrangement 152 and the fluid conduit arrangement 156 are substantially the same as those discussed above in the first two embodiments. The pump system 344 further includes a pump 348 and an adapter 360. Again, the pump 348 has similar function and mechanisms as discussed above regarding pump 148 in the first embodiment, but has a generally different shape and size, and therefore will not fit snugly within the enclosure arrangement 152. Therefore, adapter member 360 is attached to the back of the pump, and acts as the back surface of the pump 348 such that the pump may be mounted on the enclosure arrangement 152. The adapter arrangement 360 fits snugly within the enclosure arrangement 152, and covers the opening of the enclosure arrangement 152 to limit access to the chamber, and therefore the bag arrangement 20, within the enclosure arrangement 152.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A bag arrangement for containing fluid for use with a fluid pump, the bag arrangement comprising:

a bag including a first wall and an opposed second wall defining an interior chamber, the bag including a first end and a second end; and a fluid outlet port in fluid communication with the interior chamber, the port including an elongated hollow member extending through the first wall, and being oriented tangentially to the first wall;

wherein the elongated hollow member extends: along the first wall within the interior chamber adjacent and toward the first end of the bag, through the first wall, and toward the second end of the bag along an exterior of the first wall; and wherein the bag further includes a first half including the first end and a second half including the second end, wherein the port is located in the first half of the bag.

2. The bag arrangement of claim 1, wherein the first wall comprises at least two overlapping wall segments joined at a seam, and the port in the first wall is formed at the seam.

3. The bag arrangement of claim 1, wherein the hollow elongated member includes a tube including a first end within the interior chamber, a middle at an opening through the first wall, and a second end outside of the interior chamber, and wherein the second end includes a fluid conduit connector in fluid communication therewith.

4. The bag arrangement of claim 3, wherein the first end of the tube is coupled to the first wall, and wherein the middle of the tube is sealed to the first wall.

5. The bag arrangement of claim 3, wherein the fluid conduit connector comprises a Luer activated valve.

6. The bag arrangement of claim 1, wherein the first half includes a narrow portion.

7. A bag arrangement for containing fluid for use with a fluid pump, the bag arrangement comprising:

a panel defining a interior chamber, a first end and a second end;

a first half including the first end and a second half including the second end;

a fluid outlet port opening in the panel located in the first half of the bag arrangement, the outlet port opening in fluid communication with the interior chamber;

an elongated hollow member in fluid communication with the port opening, and extending in a direction from the port opening toward the second end tangentially along an exterior of the panel.

8. The bag arrangement of claim 7, wherein the elongated hollow member further extends internally into the interior chamber from the port toward the first end of the bag arrangement and tangentially along an interior of the panel.

9. The bag arrangement of claim 7, further including a second elongated member extending from the port toward the first end of the bag arrangement within the interior chamber.

10. The bag arrangement of claim 7, wherein the elongated hollow member includes a tube extending from within the interior chamber adjacent the first end of the bag arrangement, through an opening in the panel defining the port, and toward the second end of the bag arrangement along the panel.

11. The bag arrangement of claim 7, wherein the panel comprises at least two overlapping wall segments joined at a seam, and the port in the panel is formed in the seam.

12. The bag arrangement of claim 7, wherein the hollow elongated member includes a tube including a first end within the interior chamber and a second end outside of the interior chamber, and the second end includes a fluid conduit connector in fluid communication therewith.

13. The bag arrangement of claim 12, wherein the first end of the tube is coupled to the panel.

14. The bag arrangement of claim 12, wherein the fluid conduit connector comprises a Luer activated valve.

15. A pump system comprising:

an enclosure arrangement defining a chamber, the chamber accessible through an opening;

a pump mounted to the enclosure arrangement to close the opening to the chamber;

a bag arrangement containing fluid located in the chamber, the bag arrangement including:

a panel defining a interior chamber, the bag arrangement including a first end and a second end;

a first half including the first end and a second half including the second end;

a fluid outlet port opening in the panel located in the first half of the bag arrangement, the outlet port opening in fluid communication with the interior chamber; and an elongated hollow member in fluid communication with the outlet port opening, and extending from the port opening toward the second end of the bag arrangement tangentially along an exterior of the panel; and a fluid conduit arrangement in fluid communication with the elongated hollow member to complete a fluid path from the bag arrangement to the pump.

16. The pump system of claim 15, wherein the elongated hollow member further extends internally from the outlet port into the interior chamber toward the first end of the bag arrangement tangentially along an interior of the panel.

17. The pump system of claim 15, wherein the pump includes a control module, a pressure plate detachably mounted to the control module, and an adapter portion detachably mounted to the pump.

18. The pump system of claim 15, wherein the enclosure arrangement is formed of rigid material.

* * * * *